(12) United States Patent
Barajas Vélez et al.

(10) Patent No.: US 12,257,273 B2
(45) Date of Patent: Mar. 25, 2025

(54) COMPOSITIONS COMPRISING BACTERIA FOR CANCER IMMUNOTHERAPY

(71) Applicant: TRIM BIOTECH, S.L., Pamplona (ES)

(72) Inventors: Miguel Ángel Barajas Vélez, Pamplona (ES); Alfredo Resano Lizaldre, Pamplona (ES)

(73) Assignee: TRIM BIOTECH, S.L., Pamplona (ES)

( * ) Notice: Subject to any disclaimer, the term of this patent is extended or adjusted under 35 U.S.C. 154(b) by 0 days.

(21) Appl. No.: 18/257,170

(22) PCT Filed: Dec. 13, 2021

(86) PCT No.: PCT/EP2021/085474
§ 371 (c)(1),
(2) Date: Jun. 13, 2023

(87) PCT Pub. No.: WO2022/128909
PCT Pub. Date: Jun. 23, 2022

(65) Prior Publication Data
US 2024/0091276 A1    Mar. 21, 2024

(30) Foreign Application Priority Data
Dec. 14, 2020  (EP) .................................. 20383089

(51) Int. Cl.
| | |
|---|---|
| *A61K 35/74* | (2015.01) |
| *A61K 31/7004* | (2006.01) |
| *A61K 35/13* | (2015.01) |
| *A61K 39/00* | (2006.01) |
| *A61P 35/00* | (2006.01) |

(52) U.S. Cl.
CPC .......... *A61K 35/74* (2013.01); *A61K 31/7004* (2013.01); *A61K 35/13* (2013.01); *A61K 39/0011* (2013.01); *A61P 35/00* (2018.01)

(58) Field of Classification Search
CPC ..................................................... A61K 35/74
See application file for complete search history.

(56) References Cited

U.S. PATENT DOCUMENTS

| | | | | |
|---|---|---|---|---|
| 4,414,201 A | * | 11/1983 | Shionoya ................ | A61P 37/04 424/278.1 |
| 5,449,663 A | * | 9/1995 | Bicher .................... | A61P 35/00 514/23 |
| 7,253,333 B2 | * | 8/2007 | Tanaka ................. | C07K 14/715 800/9 |
| 2004/0167079 A1 | * | 8/2004 | Tidmarsh ................ | A61P 43/00 514/23 |
| 2006/0094649 A1 | * | 5/2006 | Keogh ............. | C07K 14/70503 514/19.3 |
| 2008/0241268 A1 | * | 10/2008 | Gaiger .................... | A61P 37/04 435/372.3 |

FOREIGN PATENT DOCUMENTS

| | | |
|---|---|---|
| WO | 2004/096270 | 11/2004 |
| WO | 2005/120560 | 12/2005 |

OTHER PUBLICATIONS

Jurkiewicz et al (Polski Przeglad Otorynolaryngologiczny, Tom 5, NR 2, pp. 21-25) (Year: 2016).*
Calder et al., "Glucose Metabolism in Lymphoid and Inflammatory Cells and Tissues", Current Opinion in Clinical Nutrition and Metabolic Care. vol. 10, No. 4. Jul. 1, 2007 (Jul. 1, 2007), pp. 531-540.
Fan et al., "Inactivation of Gram-Positive Bacteria by Novel Phenolic Branched-Chain Fatty Acids", Journal of Food Protection, vol. 80, No. 1, 2017, pp. 6-14, doi: 10.4315/0362-028X.JFP-16-080.
Hankaniemi et al., "Formalin Treatment Increases the Stability and Immunogenicity of Coxsackievirus B1 VLP Vaccine", Antiviral Research 171 (2019) 104595, pp. 1-9.
Levinson et al., "Production of Potent Inactivated Vaccines with Ultraviolet Irradiation: II. An Abbreviated Preliminary Report on Sterilization of Bacteria and Immunization with Rabies and St. Louis Encephalitis Vaccines", JAMA 1944; 125(8): 531-532, doi:10.1001/jama.1944.02850260005002.
Morandi et al., "A mixture of bacterial mechanical lysates is more efficient than single strain lysate and of bacterial-derived soluble products for the induction of an activating phenotype in human dendritic cells", Immunology Letters, vol. 138, No. 1, Mar. 29, 2011 (Mar. 29, 2011), pp. 86-91.
Novellino et al., "A Listing of Human Tumor Antigens Recognized by T Cells", Cancer Immunol Immunother (2005), vol. 54, pp. 187-207. DOI: 10.1007/s00262-004-0560-6.
Saeed et al., "Epigenetic Programming of Monocyte-to-Macrophage Differentiation and Trained Innate Immunity", Science 2014, vol. 345, Issue 6204, 1251086, DOI: 10.1126/science.1251086.
International Search Report and Written Opinion of International Application No. PCT/EP2021/085474, dated Mar. 11, 2022, 17 pages.

* cited by examiner

Primary Examiner — Albert M Navarro
(74) Attorney, Agent, or Firm — Chrisman Gallo Tochtrop LLC

(57) ABSTRACT

Immunogenic compositions comprising (a) a bacterial population comprising at least three pathogenic bacterial species selected from the group consisting of *Staphylococcus aureus, Streptococcus pyogenes, Streptococcus pneumoniae, Haemophilus influenzae, Klebsiella pneumoniae,* and *Moraxella catarrhalis,* wherein the bacteria are inactivated bacteria comprising the whole bacterial cell wall, and (b) one or more tumor antigenic determinants. Pharmaceutical compositions comprising the immunogenic compositions and methods for preventing and/or treating tumors in subjects in need thereof.

22 Claims, 1 Drawing Sheet

A
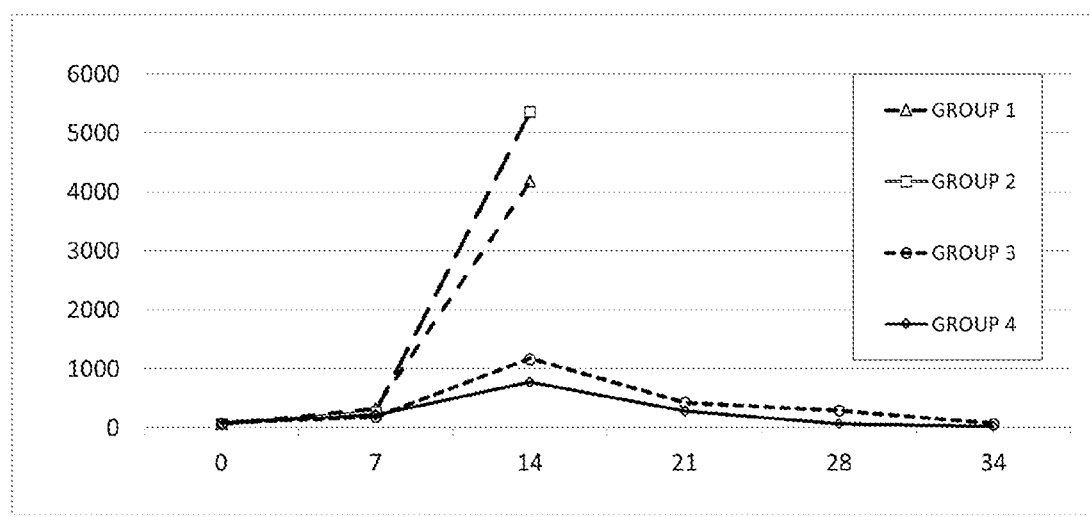
B
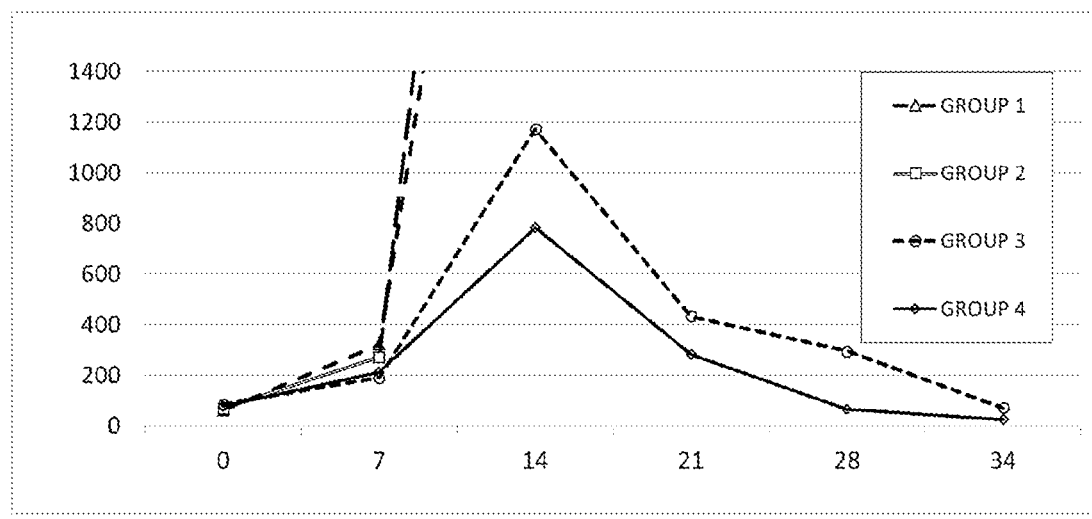

COMPOSITIONS COMPRISING BACTERIA FOR CANCER IMMUNOTHERAPY

CROSS-REFERENCE TO RELATED APPLICATIONS

This is a National Stage application of PCT international application PCT/EP2021/085474, filed on Dec. 13, 2021, which claims the benefit of European Patent Application EP20383089.8 filed Dec. 14, 2020, both of which are incorporated herein by reference in their entirety.

TECHNICAL FIELD

The invention relates to the field of cancer immunotherapy. In particular, the invention relates to immunogenic compositions comprising a combination of bacterial species for cancer treatment.

BACKGROUND ART

Malignant tumors represent one of the mayor challenges in modern medicine. It is widely accepted that conventional therapies, such as surgery, chemotherapy and radiation are of limited efficacy in many common types and stages of cancers.

Immunotherapy is an evolving area of research and an additional option for the treatment of certain types of cancers. Despite presentation of antigens by cancer cells and the presence of immune cells that could potentially react against tumor cells, it is found that, in many cases, the immune system is not well-activated against the tumor or is affirmatively suppressed. Key to this phenomenon is the ability of tumors to develop a number of immunomodulatory mechanisms to evade antitumor immune responses. The immunotherapy approach rests on the rationale that the immune system may be stimulated to identify tumor cells, and target them for destruction.

In this sense, one traditional approach has been to use inactivated bacteria as therapeutic vaccines for the treatment of malignant tumors. For example, Coley's vaccine (a combination of *Streptococcus pyogenes* and *Serratia marcescens*) has long been known to be helpful for the treatment of sarcomas and lymphomas, and BCG (*Mycobacterium bovis*) vaccine treatment has been reported to be effective for the treatment of several types of cancer.

More recently, other types of immunotherapy have been explored. For example, the use of monoclonal antibodies (mAbs) blocking immune checkpoint molecules, such as programmed cell death ligand 1 (PD-L1) and cytotoxic T-lymphocyte antigen 4 (CTLA-4), has achieved some success, highlighting the potential of immunotherapy in the oncology field. Additionally, strategies directly using immune cellular effectors, such as activated natural killer cells, chimeric antigen receptors (CAR) T-cells, tumor-infiltrating lymphocytes and tumor antigen-loaded dendritic cells, have been used to boost anti-tumor immunity. However, despite high expectations and sometimes promising results, the truth is that clinical results are often inconsistent and tumors can find escape routes that can even metastasize in the long term.

It is clear from the above that alternative immunotherapeutic approaches are needed to enhance host antitumor immunity and target tumor cells for destruction.

SUMMARY OF INVENTION

The inventors have found that a combination of inactive pathogenic bacteria is capable of generating a specific antitumoral immune response when contacted with antigens derived from tumoral cells. The present application shows that said immune response effectively slows down the growth rate of the specific tumors from which the antigens derive. The application also shows that an immunogenic composition of the invention containing said bacterial population and antigens derived from tumoral cells may even achieve disappearance of the tumor, leading to complete remission and memory responses against new challenges/relapses of the tumor.

Thus, a first aspect of the invention provides an immunogenic composition comprising: a) a bacterial population comprising at least three pathogenic bacterial species selected from the group consisting of *Staphylococcus aureus, Streptococcus pyogenes, Streptococcus pneumoniae, Haemophilus influenzae, Klebsiella pneumoniae, Staphylococcus epidermidis, Streptococcus viridans, Moraxella catarrhalis, Bordetella pertussis, Neisseria flava, Escherichia coli* and *Proteus mirabilis*, wherein the bacteria are inactivated bacteria, and (b) a tumor antigenic determinant.

Without wanting to be bound by theory the inventors hypothesise that the tumor antigens act by directing the nonspecific immune response generated by the bacterial population. Presumably, the activation of white blood cells that mediate innate immunity triggered by the pattern recognition receptors located in the bacterial cells would enhance the uptake of antigens from the tumor, turning the initially developed innate immune response towards a specific adaptive immune response against that tumor. In this sense, the inventors also found that said immune response is enhanced when the bacteria in the population retain their structural integrity, i.e. when the bacteria are whole bacteria. The immune response against the tumor is also enhanced by the particular population of bacterial species contained in the immunogenic composition of the invention.

Moreover, the inventors have also found that the immunogenic composition of the invention also generates a memory immune response against the tumor, effectively precluding relapses and/or metastasis (see example below).

A second aspect provides a method for preparing an immunogenic composition comprising contacting one or more tumor antigenic determinants with a bacterial population comprising at least three pathogenic bacterial species selected from the group consisting of *Staphylococcus aureus, Streptococcus pyogenes, Streptococcus pneumoniae, Haemophilus influenzae, Klebsiella pneumoniae, Staphylococcus epidermidis, Streptococcus viridans* and *Moraxella catarrhalis*, wherein the bacteria are inactivated bacteria.

The immunogenic composition of the invention may be prepared in situ by contacting the bacterial population with antigenic determinants obtained/derived from a tumor. In this case, it is convenient that the bacterial population is readily available, for example, as a suspension or lyophilised preparation. A third aspect of the invention thus provides a bacterial population comprising *Staphylococcus aureus, Streptococcus pyogenes, Streptococcus pneumoniae, Haemophilus influenzae, Klebsiella pneumoniae*, and *Moraxella catarrhalis*, wherein the bacteria are inactivated bacteria and comprise the whole cell wall.

The immunogenic composition of the invention may also be provided as a pharmaceutical composition ready for administration to a subject in need thereof. Thus, a fourth aspect of the invention refers to a pharmaceutical composition comprising a therapeutically effective amount of an immunogenic composition as defined in the first aspect or a bacterial population according to the third aspect of the invention together with pharmaceutically acceptable excipients and/or or carriers.

A fifth aspect of the invention provides a kit of parts comprising: (a) a bacterial population as defined in the third aspect, and, optionally, (b) instructions for its use in the preparation of an immunogenic composition of the first aspect.

A sixth aspect provides for the use of the bacterial population of the third aspect of the invention or the kit of parts of the fifth aspect of the invention for preparing an immunogenic composition as defined in the first aspect of the invention.

A seventh aspect provides an immunogenic composition as defined in the first aspect of the invention or the pharmaceutical composition comprising said immunogenic composition as defined in the fourth aspect of the invention for use as a medicament. This can be rephrased as the use of an immunogenic composition as defined in the first aspect of the invention or a pharmaceutical composition comprising said immunogenic composition as defined in the fourth aspect of the invention for the preparation of a medicament. The invention also discloses a method for preventing and/or treating a subject in need thereof, the method comprising administering an immunogenic composition as defined in the first aspect of the invention or a pharmaceutical composition comprising said immunogenic composition as defined in the fourth aspect of the invention.

An eight aspect of the invention provides an immunogenic composition as defined in the first aspect of the invention or a pharmaceutical composition comprising said immunogenic composition as defined in the fourth aspect of the invention for use in a method for the prevention and/or treatment of a tumor. This can be rephrased as the use of an immunogenic composition as defined in the first aspect of the invention or a pharmaceutical composition comprising said immunogenic composition as defined in the fourth aspect of the invention for the preparation of a medicament for the prevention and/or treatment of a tumor. The invention also discloses a method for preventing and/or treating a tumor, the method comprising administering an immunogenic composition as defined in the first aspect of the invention or a pharmaceutical composition comprising said immunogenic composition as defined in the fourth aspect of the invention to a subject in need thereof.

In a ninth aspect, the present invention provides an immunogenic composition as defined in the first aspect of the invention or a pharmaceutical composition comprising said immunogenic composition as defined in the fourth aspect of the invention for use in combination therapy with surgery, radiation or an antitumoral agent for the prevention and/or treatment of a tumor. This aspect can also be formulated as the use of an immunogenic composition as defined in the first aspect of the invention or a pharmaceutical composition comprising said immunogenic composition as defined in the fourth aspect of the invention for the manufacture of a medicament for the prevention and/or treatment of a tumor in combination therapy with surgery, radiation or an antitumoral agent. This aspect can also be formulated as a method for preventing and/or treating a tumor, the method comprising administering an immunogenic composition as defined in the first aspect of the invention or a pharmaceutical composition comprising said immunogenic composition as defined in the fourth aspect of the invention, in combination with surgery, radiation or an antitumoral agent, to a subject in need thereof.

Furthermore, the inventors have surprisingly found that the bacterial population consisting of *Staphylococcus aureus, Streptococcus pyogenes, Streptococcus pneumoniae, Haemophilus influenzae, Klebsiella pneumoniae,* and *Moraxella catarrhalis,* wherein the bacteria are inactivated bacteria, is effective in the treatment of tumors of the colon. Thus, a tenth aspect of the invention provides for a bacterial population consisting of *Staphylococcus aureus, Streptococcus pyogenes, Streptococcus pneumoniae, Haemophilus influenzae, Klebsiella pneumoniae,* and *Moraxella catarrhalis,* wherein the bacteria are inactivated bacteria, for use in the prevention and/or treatment of a tumor of the gastrointestinal tract, nervous system, hematopoietic system, reproductive system (such as cervical, ovarian, uterine, vaginal, and vulvar), urinary tract, endocrine system, skin, heart, brain, eyes, testes, muscles, bones or breasts. This aspect can also be formulated as the use of a bacterial population consisting of *Staphylococcus aureus, Streptococcus pyogenes, Streptococcus pneumoniae, Haemophilus influenzae, Klebsiella pneumoniae,* and *Moraxella catarrhalis,* wherein the bacteria are inactivated bacteria, for the manufacture of a medicament for the prevention and/or treatment of a tumor of the gastrointestinal tract, nervous system, hematopoietic system, reproductive system (such as cervical, ovarian, uterine, vaginal, and vulvar), urinary tract, endocrine system, skin, heart, brain, muscles, eyes, testes, bones or breasts. This aspect can also be formulated as a method for preventing and/or treating a tumor of the gastrointestinal tract, nervous system, hematopoietic system, reproductive system (such as cervical, ovarian, uterine, vaginal, and vulvar), urinary tract, endocrine system, skin, heart, brain, eyes, testes, muscles, bones or breasts, the method comprising administering a bacterial population consisting of *Staphylococcus aureus, Streptococcus pyogenes, Streptococcus pneumoniae, Haemophilus influenzae, Klebsiella pneumoniae,* and *Moraxella catarrhalis,* wherein the bacteria are inactivated bacteria, to a subject in need thereof.

An eleventh aspect of the invention refers to a bacterial population as defined in the third aspect or a pharmaceutical composition comprising the same as defined in the fourth aspect for use in the prevention and/or treatment of a tumor, wherein the prevention and/or treatment comprises simultaneous, sequential or separate administration within a therapeutic interval of the bacterial population and one or more tumor antigenic determinants. This can be rephrased as the use of a bacterial population as defined in the third aspect or a pharmaceutical composition comprising the same as defined in the fourth aspect for the preparation of a medicament for the prevention and/or treatment of a tumor, wherein said medicament is administered simultaneously, sequentially or separately within a therapeutic interval with one or more tumor antigenic determinants. The invention also discloses a method for preventing and/or treating a tumor, said method comprising administering to a subject in need thereof a therapeutically effective amount of a bacterial population as defined in the third aspect or a pharmaceutical composition comprising the same as defined in the fourth aspect in combination with one or more tumor antigenic determinants, wherein the bacterial population and the one or more tumor antigenic determinants are administered simultaneously, sequentially or separately within a therapeutic interval.

BRIEF DESCRIPTION OF DRAWINGS

FIG. 1. A: Measurement of the volume of CT-26 tumors implanted subcutaneously in 12-week-old Balb/c mice. The 4 experimental groups tested are shown (n=5 mice/group): Group 1—control, Group 2—bacterial population, Group 3—immunogenic composition, group 4—immunogenic composition with glucose. B: Detail of the antitumor activity observed in experimental groups 3 and 4 (n=5 mice/group).

The X-axis shows the variable "time", indicating the days that have elapsed since the start of treatment. The Y axis shows the variable "tumor size", indicating the volume (cm 3) that tumors acquire from the start of treatment.

DETAILED DESCRIPTION OF THE INVENTION

All terms as used herein in this application, unless otherwise stated, shall be understood in their ordinary meaning as known in the art. Other more specific definitions for certain terms as used in the present application are as set forth below and are intended to apply uniformly through-out the specification and claims unless an otherwise expressly set out definition provides a broader definition.

A "cancer", as used herein, is any unwanted growth of cells serving no physiological function. In general, a cancer cell has been released from its normal cell division control, i.e., a cell whose growth is not regulated by the ordinary biochemical and physical influences in the cellular environment. Thus, "cancer" is a general term for diseases characterized by abnormal uncontrolled cell growth. In most cases, a cancer cell proliferates to form clonal cells that are either benign or malignant. The resulting lump or cell mass, or "tumor," is generally capable of invading and destroying surrounding normal tissues. By "malignant tumor" is meant an abnormal growth of any cell type or tissue, that has a deleterious effect in the organism having the abnormal growth. The term "malignancy" or "cancer" includes cell growths that are technically benign but which carry the risk of becoming malignant. Tumoral cells may spread from their original site to other parts of the body through the lymphatic system or blood stream in a process known as "metastasis" causing a "secondary tumor" that results in "metastatic cancer" disease.

An "immunogenic composition" is a composition that, when administered to subject, elicits, or is able to elicit, directly or indirectly, an immune response in the subject.

"Trained immunity" is a new emerging concept that defines the ability of the innate immune system to generate immune memory and provide long-lasting protection against pathogens. It implies the adaptation of innate immunity processes in a de-facto innate immunological memory though mechanisms that involves epigenetic changes in cells involved in the innate immune system (Saeed et al, Science 2014)). It is thought that trained immunity provides protection by (i) increasing the nonspecific effector response of innate immune cells (e.g., monocyte/macrophages) and (ii) harnessing the activation state of dendritic cells to enhance adaptive T cell responses to both specific and nonrelated (bystander) antigens. In the context of the present invention the composition of the invention, containing both pathogen-associated molecular patterns from selected bacterial species and antigenic determinants of a particular tumor, elicits such a trained immune response to target the particular type of tumor.

"Pathogen-associated molecular patterns" are small molecular motifs on the surface of microbes that are recognized by pattern recognition receptors in the host, thereby activating innate immune responses in the host.

In the sense of the present invention "bacteria that comprise the whole bacterial cell wall" is understood as bacteria that are "whole", meaning that they retain the integrity of their cell wall, where the pathogen-associated molecular patterns are contained. Throughout the present disclosure the expression "bacteria that comprise the whole bacterial cell wall" and "whole" bacteria are used interchangeably. On the contrary, "lysed bacteria" are those that do not retain the integrity of their cell wall, i.e., bacteria that are broken.

An "antigen" is a molecule or molecular structure, usually present in the surface of a cell, that is capable of specifically interacting with an antigen recognition molecule of the immune system triggering an immune response. The term "antigenic determinant", also called "epitope", is the part of an antigen that is recognized by the antigen recognition molecule.

An "adjuvant" is an agent that acts in a non-specific manner to increase the immune response.

The term "vaccine" refers to an immunogenic composition accompanied by adequate excipients and/or carriers, that when administered to a subject, elicits, or is able to elicit, directly or indirectly, a protective immune response against the pathogen for which it was designed".

As used herein, the term "subject" or "host" is intended for the target individuals in need thereof to whom the immunogenic composition of the invention are administered, among others humans, mammals, livestock, or any other animal species susceptible to be treated with the compositions of the invention. In most embodiments of the invention the subject is a human.

The expression "therapeutically effective amount" as used herein, refers to the amount of the immunogenic composition of the invention that, when administered, is sufficient to prevent development of, or alleviate to some extent, one or more of the symptoms of the disease which is addressed. The particular dose of agent administered according to this invention will of course be determined by the particular circumstances surrounding the case, including the amount of agent administered, the route of administration, the particular condition being treated, and the similar considerations.

The expression "pharmaceutical composition" encompasses both compositions intended for human as well as for non-human animals (i.e. veterinarian compositions).

The expression "pharmaceutically acceptable carriers or excipients" refers to pharmaceutically acceptable materials, compositions or vehicles. Each component must be pharmaceutically acceptable in the sense of being compatible with the other ingredients of the pharmaceutical composition. It must also be suitable for use in contact with the tissue or organ of humans and non-human animals without excessive toxicity, irritation, allergic response, immunogenicity or other problems or complications commensurate with a reasonable benefit/risk ratio.

When percentages are indicated in the present disclosure, they usually refer to percentage weight per weight (% w/w), unless the composition is liquid, in which case the percentage refers to percentage weight per volume. % w/w or % w/v of a component refers to the amount of the single component relative to the total weight or volume of the composition.

As mentioned above, the inventors have found that an immunogenic composition as disclosed in the first aspect of the invention is effective for the prevention and treatment of tumors. It has been hypothesized that, when administered to a cancer patient, the judicious combination of inactive bacteria selected from the group consisting of *Staphylococcus aureus, Streptococcus pyogenes, Streptococcus pneumoniae, Haemophilus influenzae, Klebsiella pneumoniae, Staphylococcus epidermidis, Streptococcus viridans* and *Moraxella catarrhalis* generates a relevant innate immune response which, in the presence of tumoral antigenic determinants, is conveniently directed to the tumoral cells. This trained immunity counteracts the immunomodulatory mechanisms that allow the tumoral cells to escape from the immune system, such that tumor cells are targeted for destruction.

The Bacterial Population

The inventors have found an optimal combination of pathogenic bacteria to include in the immunogenic composition. The selection of bacterial species is very important to adequately stimulate the immune system in the sense of the present invention. It is known that pathogens contain pathogen-associated molecular patterns in their surface which are recognized by pattern recognition receptors in the host. However, arriving at an optimal combination of signals is not an easy task.

In some embodiments of the first aspect of the invention the bacterial population comprises at least four or at least five bacterial species selected from the group consisting of *Staphylococcus aureus, Streptococcus pyogenes, Streptococcus pneumoniae, Haemophilus influenzae, Klebsiella pneumoniae, Staphylococcus epidermidis, Streptococcus viridans* and *Moraxella catarrhalis*. In other embodiments the bacterial population comprises at least three or at least four species selected from the group consisting of *Staphylococcus aureus, Streptococcus pyogenes, Streptococcus pneumoniae, Haemophilus influenzae, Klebsiella pneumoniae* and *Moraxella catarrhalis*.

In one particular embodiment the bacterial population comprises all five of 20 *Staphylococcus aureus, Streptococcus pyogenes, Streptococcus pneumoniae, Haemophilus influenzae, Klebsiella pneumoniae* and *Moraxella catarrhalis*. In another particular embodiment the bacterial population consists of *Staphylococcus aureus, Streptococcus pyogenes, Streptococcus pneumoniae, Haemophilus influenzae, Klebsiella pneumoniae* and *Moraxella catarrhalis*.

The formulation of the bacterial population is also relevant. Although variable to some extent, the proportion of each species in the bacterial population may influence the immune response and the inventors have found the best formulations to attain the desired effect. In some embodiments of the first aspect of the invention the bacterial population has the following composition: from 5 to 25% of *Staphylococcus aureus*, from 1 to 20% of *Streptococcus pyogenes*, from 15 to 70% of *Streptococcus pneumoniae*, from 1 to 30 of *Haemophilus influenzae*, from 1 to 20% of *Klebsiella pneumoniae*, and from 1 to 25 of *Moraxella catarrhalis*, wherein the sum of the percentages for the species in the bacterial population is 100.

In some embodiments of the first aspect of the invention the bacterial population has the following composition: from 5 to 25% of *Staphylococcus aureus*, from 1 to 20% of *Streptococcus pyogenes*, from 15 to 50% of *Streptococcus pneumoniae*, from 10 to 30% of *Haemophilus influenzae*, from 1 to 20% of *Klebsiella pneumoniae*, and from 5 to 25% of *Moraxella catarrhalis*, wherein the sum of the percentages for the species in the bacterial population is 100.

In other embodiments, the bacterial population has the following composition: from 10 to 20% of *Staphylococcus aureus*, from 5 to 15% of *Streptococcus pyogenes*, from 20 to 40% of *Streptococcus pneumoniae*, from 15 to 25% of *Haemophilus influenzae*, from 5 to 15% of *Klebsiella pneumoniae*, and from 10 to 20% of *Moraxella catarrhalis*, wherein the sum of the percentages for the species in the bacterial population is 100. In a particular embodiment the bacterial population has the following composition: 15% of *Staphylococcus aureus*, 10% of *Streptococcus pyogenes*, 30% of *Streptococcus pneumoniae*, 20% of *Haemophilus influenzae*, 10% of *Klebsiella pneumoniae*, and 15% of *Moraxella catarrhalis*.

Furthermore, the inventors have found that use of whole bacterial cells, which maintain the structural integrity of the cell, achieves better results in the context of the present invention that the use of lysed bacterial cells. Therefore, in a particular embodiment, the inactivated bacteria comprise the whole bacterial cell wall. In another embodiment, the inactivated bacteria maintain the structural integrity of the bacterial cell wall. Methods to inactivate pathogenic bacteria while retaining the structural integrity of the bacterial cell are known in the art. Non limiting examples of these inactivation methods are phenolization, irradiation and formalin or formaldehyde treatment (Fan et at, J Food Prot 2017; Levinson et al., JAMA 1944; Hankaniemi et al, Antiviral Research 2019). In a particular embodiment, the bacterial cells present in the immunogenic composition of the invention have been inactivated by treatment with phenol. This may be achieved, for example, by treating the bacteria with phenol 0.5% (w/v) during 12 h at room temperature.

Some aspects of the present invention are referred to the bacterial population per se, which is essential and particularly designed for preparing the immunogenic composition of the first aspect of the invention. In particular embodiments, the bacteria in said bacterial population are whole bacteria. In particular embodiments the bacteria in the bacterial population have been inactivated by phenolization. In particular embodiments the bacteria in the combination maintain the structure and integrity of the cell wall.

Further, in particular embodiments, the bacterial population comprises whole inactive cells of *Staphylococcus aureus, Streptococcus pyogenes, Streptococcus pneumoniae, Haemophilus influenzae, Klebsiella pneumoniae* and *Moraxella catarrhalis*. In particular embodiments the bacterial population consists of whole inactive cells of *Staphylococcus aureus, Streptococcus pyogenes, Streptococcus pneumoniae, Haemophilus influenzae, Klebsiella pneumoniae* and *Moraxella catarrhalis*. In particular embodiments the bacterial population has the following composition: from 5 to 25% of *Staphylococcus aureus*, from 1 to 20% of *Streptococcus pyogenes*, from 15 to 50% of *Streptococcus pneumoniae*, from 10 to 30% of *Haemophilus influenzae*, from 1 to 20% of *Klebsiella pneumoniae*, and from 5 to 25% of *Moraxella catarrhalis*, wherein the sum of the percentages for the species in the bacterial population is 100 and the bacterial cells are whole and inactive. In other particular embodiments the bacterial population has the following composition: from 10 to 20% of *Staphylococcus aureus*, from 5 to 15% of *Streptococcus pyogenes*, from 20 to 40% of *Streptococcus pneumoniae*, from 15 to 25% of *Haemophilus influenzae*, from 5 to 15% of *Klebsiella pneumoniae*, and from 10 to 20% of *Moraxella catarrhalis*, wherein the sum of the percentages for the species in the bacterial population is 100 and the bacterial cells are whole and inactive. In a particular embodiment the bacterial population has the following composition: 15% of *Staphylococcus aureus*, 10% of *Streptococcus pyogenes*, 30% of *Streptococcus pneumoniae*, 20% of *Haemophilus influenzae*, 10% of *Klebsiella pneumoniae*, and 15% of *Moraxella catarrhalis*, wherein the bacterial cells are whole and inactive.

The bacterial population may be provided, for example, as a suspension or dehydrated preparation. The dehydration can be carried out by a lyophilization process. In some embodiments the bacterial population is a lyophilised preparation. In other embodiments the bacterial population is provided as a suspension.

Further, additives or other additional compounds may be added to the bacterial population to protect the bacterial cells from being damaged. As such, the invention also refers to a bacterial composition comprising the bacterial population as described above. Appropriate additives for the bacterial composition are preservatives, adjuvants, processing aids, cryoprotectants, antioxidants, etc. . . . Again, the bacterial compositions may be provided as a dehydrated (for instance, freeze-dried) compositions or as suspensions. In one embodiment the bacterial composition is lyophilised and contains a cryoprotectant, such as glycerol, sucrose or trehalose.

The bacterial populations may be prepared by mixing appropriate proportions of the desired species. The bacterial species are available to the public. For example, the bacterial species may be obtained from specialized companies or from deposit institutions. The desired bacterial population may also be delivered (in the desired proportions) by specialized commercial sources. Companies such as Diater are appropriate commercial sources. Other possible commercial sources for the bacterial population are Roxall, Inmunotek and Allergy Therapeutics.

The invention also provides a kit of parts that that comprises a bacterial population or a bacterial composition as described above. In particular embodiments, the kit also contains instructions for its use in the preparation of an immunogenic composition of the first aspect. All embodiments mentioned above for the bacterial population or bacterial composition also apply to the kit of parts.

The invention also provides for the use of the bacterial population or the bacterial composition or the kit of parts as described above for preparing an immunogenic composition as defined in the first aspect of the invention.

The Antigenic Determinants

The immunogenic composition according to the first aspect of the invention contains antigenic determinants from a tumor. In most embodiments the tumor is a malignant tumor. Said antigenic determinants may be contained in pure, isolated antigens or in tumoral cells. In some embodiments the antigenic determinant is in the form of tumoral cells. This has the advantage that the immunogenic composition may contain, not only one, but several antigenic determinants that are characteristic of a certain type of tumor, thus improving the chances of immune activation to target that particular type of tumor.

The tumor cells may be provided by performing a biopsy of tumor(s). The tumor cells may derive from only one subject (one tumor) or from a pool of biopsied cells of the same type of tumor. The tumor cells may also be obtained from a tumoral cell line.

In some embodiments the immunogenic determinant is in the form of whole tumor cells. This is understood as tumor cells that contain the whole cell membrane, particularly cells that maintain the structural integrity of the cell membrane. This may have the advantage of enhanced interaction with the antigen presenting cells. In this case, the cells must be inactivated by methods that do not destroy the structural integrity of the cell (see above). In other embodiments, the immunogenic determinant is in the form of a tumor cell lysate. This has the advantage of guaranteeing non-proliferation of the tumor cells as well as ease of use. Non-limiting methods for cell lysis are temperature treatment (i.e. freeze-thaw and/or heat treatments), high-pressure treatment, ultrasonic treatment, mechanical treatment, all of which are well known in the art. For example, the tumor lysate may be obtained by subjecting the tumor cells to a procedure consisting of 3 cycles of freezing ($-80°$ C.) and thawing ($37°$ C.). Other non-limiting methods are based in suspending the cells in hypotonic solution (osmotic lysis) and/or by using chemicals (e.g. antibiotics, chelating agents, detergents and/or solvents) that can interact with certain components of the cell wall and allow the inner components to leak through the cell wall.

The antigenic determinant may also be in the form of a pure, isolated antigen or combination of pure, isolated antigens. This has the advantage of greater versatility and scalability. Relevant Tumor-Associated Antigens have been disclosed, for example, in Novellino, et al, Cancer Immunol Immunother 2005. The trained immune response can be directed to several types of tumors for which the selected antigen or antigens are predominant. The immunogenic compositions can also comprise a cocktail with selected antigens from several tumors, thus allowing treating different tumors with the same immunogenic composition. This requires that predominant antigens are identified. For example, in one embodiment the immunogenic composition may contain an antigen selected from the group consisting of AFP, CEA, HER-2, p53, WT1, and combinations thereof.

Adjuvants

The immunogenic compositions of the invention may contain additional compounds. In particular embodiments, the immunogenic composition of the invention may also contain a compound selected from a monosaccharide, an amino acid, a fatty acid, a substrate or metabolite of the Krebs cycle, a beta-glucan, a ketonic body, lactate, glyceraldehyde, glycerol, glutamate, and a combination thereof. As shown in the example below, the inventors have found that supplementation of the immunogenic compositions of the invention enhances the immunogenic response, thereby improving the effectiveness of the treatment (greater reduction in tumor size/eradication of the tumor and virtually precluding metastasis). It is hypothesized that these compounds are nutrients that allow monocytes and macrophages to become activated and with sufficient energy resources to initiate the innate immune response induced by the immunogenic composition. These compounds may be considered as adjuvants.

Non-limiting examples of the compounds above are glucose, fructose, glyceraldehyde, lactate, pyruvate, oxalate, malate, glutamate, fumarate, alpha-ketoglutarate, succinate, citrate, glycerol, glutamine, arginine, ketonic bodies, beta-glucans, monounsaturated fatty acids and polyunsaturated fatty acids, and combinations thereof. In particular embodiments, the immunogenic composition of the invention further comprises a compound selected from the group consisting of glucose, fructose, glutamine, arginine, malate, glutamate, and combinations thereof. In another particular embodiment the immunogenic composition of the invention further comprises glucose.

The present application also discloses a compound selected from a monosaccharide, an amino acid, a fatty acid, a substrate or metabolite of the Krebs cycle, a beta-glucan, a ketonic body, lactate, glyceraldehyde, glycerol, glutamate, and a combination thereof as an immunogenic adjuvant. Also disclosed is use of a compound selected from a monosaccharide, an amino acid, a fatty acid, a substrate or metabolite of the Krebs cycle, a beta-glucan, a ketonic body, lactate, glyceraldehyde, glycerol, glutamate, and a combination thereof in the preparation of vaccines or immunogenic compositions. Also disclosed is the use of a compound selected from a monosaccharide, an amino acid, a fatty acid, a substrate or metabolite of the Krebs cycle, a beta-glucan, a ketonic body, lactate, glyceraldehyde, glycerol, glutamate, and a combination thereof for stimulating the activity of antigen presenting cells. Also disclosed is the use of a compound selected from a monosaccharide, an amino acid, a fatty acid, a substrate or metabolite of the Krebs cycle, a beta-glucan, a ketonic body, lactate, glyceraldehyde, glycerol, glutamate, and a combination thereof for enhancing a trained immune response in a subject. In particular, the compound selected from glucose, fructose, glyceraldehyde, lactate, pyruvate, oxalate, malate, glutamate, fumarate, alpha-ketoglutarate, succinate, citrate, glycerol, glutamine, arginine, ketonic bodies, beta-glucans, monounsaturated fatty acids, polyunsaturated fatty acids, and combinations thereof, for example, glucose, fructose, glutamine, arginine, malate, glutamate, and combinations thereof. In a particular, said compound is glucose.

The amount of the compound as defined above, for example, glucose, in the immunogenic composition or pharmaceutical composition of the invention may be from 0.5 to 10%. In some embodiments, said amount is from 1 to 10%, for example 1, 2, 3, 4, 5, 6, 7, 8, 9 or 10%. In a particular embodiment the amount of the compound in the immunogenic composition or pharmaceutical composition of the invention is 5%.

The immunogenic composition of the invention may also contain traditional adjuvants. Non-limiting adjuvants for use in the immunogenic compositions of the invention are inorganic compounds, such as alum, aluminium hydroxide, aluminium phosphate and calcium phosphate hydroxide, mineral oils, such as paraffin oil, toxoids, squalene, detergents, such as Quil A, cytokines, such as IL-1, IL-2, IL-12, Freund's complete adjuvant, Freund's incomplete adjuvant.

Preparation of the Immunogenic Composition

As mentioned above, the immunogenic composition of the invention may be prepared in situ by contacting the bacterial population with antigenic determinants from a tumor. This may be the case, for example, for autologous treatments where the immunogenic composition contains tumoral cells or a cell lysate obtained from the subject to be treated. In this case, it is convenient that the bacterial population is readily available, for example, as a suspension or lyophilised preparation.

The antigenic determinant may be as disclosed above. For example, in some embodiments, the method for preparing the immunogenic composition contemplates providing tumor cells obtained from a patient's tumor, or from tumors of the same type from several patients (pool of tumoral cells), or from a tumoral cell line, and inactivating said tumoral cells. Thus, in one embodiment, the method for preparing the immunogenic composition of the invention comprises the following steps: (i) inactivating tumor cells, and (ii) contacting the inactivated tumor cells of step (i) with a bacterial population as defined above. In some embodiments the cells are inactivated by a method that maintains the structural integrity of the cell membrane, such as irradiation or phenolization. In some embodiments, the method for preparing the immunogenic composition contemplates providing tumor cell lysate. Appropriate methods for lysing the cells have been disclosed above. For example, the tumor lysate may be obtained by subjecting the sample obtained from tumor tissue or from a cell line to a procedure consisting of 3 cycles of freezing (−80° C.) and thawing (37° C.). In particular embodiments the method for preparing the immunogenic composition includes adding an additional compound, such as a compound selected from glucose, fructose, glyceraldehyde, lactate, pyruvate, oxalate, malate, glutamate, fumarate, alpha-ketoglutarate, succinate, citrate, glycerol, glutamine, arginine, ketonic bodies, beta-glucans, monounsaturated fatty acids, polyunsaturated fatty acids, and combinations thereof, for example, glucose, fructose, glutamine, arginine, malate, glutamate, and combinations thereof, in particular, glucose.

In still a further embodiment the immunogenic composition may be prepared by contacting pure, isolated tumoral antigens with a bacterial population as defined above, and optionally adding a compound selected from glucose, fructose, glyceraldehyde, lactate, pyruvate, oxalate, malate, glutamate, fumarate, alpha-ketoglutarate, succinate, citrate, glycerol, glutamine, arginine, ketonic bodies, beta-glucans, monounsaturated fatty acids, polyunsaturated fatty acids, and combinations thereof, for example, glucose, fructose, glutamine, arginine, malate, glutamate, and combinations thereof, in particular, glucose. The contacting step may be performed at room temperature and kept on ice until use. The contacting may be performed by gentle mixing, for example, by pipetting. In one particular example, the immunogenic composition may be prepared by mixing by pipetting the antigenic determinants (for example, the tumor lysate obtained from lysing around 0.5×10e6 tumor cells) with around 50 uL of bacterial population (10e8/mL) at room temperature.

Pharmaceutical Compositions

Another aspect of the invention refers to a pharmaceutical composition comprising a therapeutically effective amount of an immunogenic composition as defined above together with pharmaceutically acceptable excipients and or carriers. The present application also discloses pharmaceutical composition comprising a therapeutically effective amount of a bacterial population as defined above together with pharmaceutically acceptable excipients and or carriers. The pharmaceutical compositions of the invention may be considered as vaccines. Thus this aspect can also be worded as a vaccine comprising a therapeutically effective amount of an immunogenic composition as defined above together with pharmaceutically acceptable excipients and or carriers. Also disclosed are vaccines comprising a therapeutically effective amount of a bacterial population as defined above together with pharmaceutically acceptable excipients and or carriers.

The relative amounts of bacterial population, immunogenic determinants, the pharmaceutically acceptable excipients, and/or any additional ingredients in a pharmaceutical composition of the invention will vary, depending upon the identity, size, and/or condition of the subject treated and further depending on the route by which the composition is to be administered.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Excipients such as coloring agents, coating agents, sweetening, and flavouring agents can be present in the composition, according to the judgment of the formulator.

The pharmaceutical compositions containing the immunological compositions of the invention can be presented in any dosage form, for example, solid or liquid, and can be administered by any suitable route, for example, oral, parenteral, rectal, topical, intranasal or sublingual route, for which they will include the pharmaceutically acceptable excipients necessary for the formulation of the desired dosage form, for example, topical formulations (ointment, creams, lipogel, hydrogel, etc.), eye drops, aerosol sprays, injectable solutions, osmotic pumps, etc.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, corn-starch, powdered sugar, and combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked polyvinylpyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and combinations thereof.

Exemplary binding excipients include, but are not limited to, starch (e.g., corn-starch and starch paste); gelatin; sugars (e.g., sucrose, glucose, dextrose, dextrin, molasses, lactose, lactitol, mannitol); natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, polyvinylpyrrolidone), magnesium aluminium silicate (Veegum), and larch arabogalactan); alginates; polyethylene oxide; polyethylene glycol; inorganic calcium salts; silicic acid; polymethacrylates; waxes; water; alcohol; and combinations thereof.

Exemplary preservatives may include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, ascorbyl palmitate, ascorbyl stearate, ascorbyl oleate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and combinations thereof.

In one embodiment the pharmaceutical composition of the invention is a parenteral composition. In one embodiment the pharmaceutical composition of the invention is an intradermal composition. In another embodiment the pharmaceutical composition of the invention is a transdermal composition. In another embodiment the pharmaceutical composition of the invention is an intravenous composition. In another embodiment the pharmaceutical composition of the invention is a sublingual composition. In another embodiment the pharmaceutical composition of the invention is a subcutaneous composition. In another embodiment the pharmaceutical composition of the invention is an oral composition. In another embodiment the pharmaceutical composition of the invention is a nasopharyngeal composition.

In one embodiment the pharmaceutical composition comprises from 10e7 to 10e12 inactivated bacterial cells/dose. In one embodiment the pharmaceutical composition comprises from 10e8 to 10e11 inactivated bacterial cells/dose, for example 10e8, 10e9 or 10e10 inactivated bacterial cells/dose.

In some embodiments, the pharmaceutical composition of the invention comprises and adjuvant. In a particular embodiment the pharmaceutical composition of the invention comprises a compound selected from glucose, fructose, glyceraldehyde, lactate, pyruvate, oxalate, malate, glutamate, fumarate, alpha-ketoglutarate, succinate, citrate, glycerol, glutamine, arginine, ketonic bodies, beta-glucans, monounsaturated fatty acids, polyunsaturated fatty acids, and combinations thereof. In other particular embodiments, the pharmaceutical composition of the invention comprises a compound selected from the group consisting of glucose, fructose, glutamine, arginine, malate, glutamate, and combinations thereof. In a particular embodiment the pharmaceutical composition of the invention comprises glucose.

Therapeutical Uses

The eight to eleventh aspects of the invention refer to therapeutical use of the compositions of the invention in prevention and/or treatment of tumors. In most embodiments, the tumors to be treated are malignant tumors. Therefore, the present application inherently refers to the prevention and/or treatment of cancer.

As mentioned above, it is hypothesized that the activation of white blood cells that mediate innate immunity triggered by the pattern recognition receptors located in the bacterial cells enhance the uptake of antigens from the tumor, turning the initially developed innate immune response towards a specific adaptive immune response against that tumor. Said white blood cells that mediate innate immunity include antigen presenting cells, such as monocytes, macrophages and dendritic cells, basophils, eosinophils, Langerhans cells, mast cells, neutrophils, NK and NKT cells.

Also disclosed is an immunogenic composition as defined in the first aspect of the invention or a bacterial population as defined in the third aspect or a pharmaceutical composition as defined in the fourth aspect of the invention for use in eliciting a trained innate immune response against a tumor. This can be rephrased as an immunogenic composition as defined in the first aspect of the invention or a bacterial population as defined in the third aspect or a pharmaceutical composition as defined in the fourth aspect of the invention for use in the preparation of a medicament for eliciting a trained innate immune response against a tumor in a subject in need thereof. Also disclosed is a method for eliciting a trained innate immune response against a tumor, the method comprising administering an immunogenic composition as defined in the first aspect of the invention or a bacterial population as defined in the third aspect or a pharmaceutical composition as defined in the fourth aspect of the invention in a subject in need thereof.

The present application also discloses an immunogenic composition as defined in the first aspect of the invention or a bacterial population as defined in the third aspect or a pharmaceutical composition as defined in the fourth aspect of the invention for use in increasing the nonspecific effector response of white blood cells that mediate innate immunity. This can be rephrased as an immunogenic composition as defined in the first aspect of the invention or a bacterial population as defined in the third aspect or a pharmaceutical composition as defined in the fourth aspect of the invention for use in the preparation of a medicament for increasing the nonspecific effector response of white blood cells that mediate innate immunity. Also disclosed is a method for increasing the nonspecific effector response of white blood cells that mediate innate immunity, the method comprising administering an immunogenic composition as defined in the first aspect of the invention or a bacterial population as defined in the third aspect or a pharmaceutical composition as defined in the fourth aspect of the invention, to a subject in need thereof. In some embodiments, said white blood cells that mediate immunity are selected from antigen presenting cells, such as monocytes, macrophages and dendritic cells, basophils, eosinophils, Langerhans cells, mast cells, neutrophils, NK and NKT cells, in particular they are selected from monocytes, macrophages and dendritic cells.

The present application also discloses a bacterial population as defined in the third aspect or a pharmaceutical composition comprising the same as defined in the fourth aspect for use in eliciting a trained innate immune response against a tumor, wherein the eliciting a trained innate immune response comprises simultaneous, sequential or separate administration within a therapeutic interval of the bacterial population and one or more tumor antigenic determinants. This can be rephrased as the use of a bacterial population as defined in the third aspect or a pharmaceutical composition comprising the same as defined in the fourth aspect for the preparation of a medicament for eliciting a trained innate immune response against a tumor, wherein said medicament is administered simultaneously, sequentially or separately within a therapeutic interval with one or more tumor antigenic determinants. The invention also discloses a method for eliciting a trained innate immune response against a tumor, said method comprising administering to a subject in need thereof a therapeutically effective amount of a bacterial population as defined in the third aspect or a pharmaceutical composition comprising the same as defined in the fourth aspect in combination with one or more tumor antigenic determinants, wherein the bacterial population and the one or more tumor antigenic determinants are administered simultaneously, sequentially or separately within a therapeutic interval.

The present application also discloses a bacterial population as defined in the third aspect or a pharmaceutical composition comprising the same as defined in the fourth aspect for use in increasing the nonspecific effector response of white blood cells that mediate innate immunity, wherein the increasing the nonspecific effector response comprises simultaneous, sequential or separate administration within a therapeutic interval of the bacterial population and one or more tumor antigenic determinants. This can be rephrased as the use of a bacterial population as defined in the third aspect or a pharmaceutical composition comprising the same as defined in the fourth aspect for the preparation of a medicament for increasing the nonspecific effector response of white blood cells that mediate innate immunity, wherein said medicament is administered simultaneously, sequentially or separately within a therapeutic interval with one or more tumor antigenic determinants. The invention also discloses a method for increasing the nonspecific effector response of white blood cells that mediate innate immunity, said method comprising administering to a subject in need thereof a therapeutically effective amount of a bacterial population as defined in the third aspect or a pharmaceutical composition comprising the same as defined in the fourth aspect in combination with one or more tumor antigenic determinants, wherein the bacterial population and the one or more tumor antigenic determinants are administered simultaneously, sequentially or separately within a therapeutic interval.

The tumor which can be prevented or treated by use of the immunogenic composition of the invention is not particularly limited, so long as tumoral cells or antigens from the tumor are available. Non-limiting types of tumors that can be prevented or treated in the sense of the present invention are carcinomas, sarcomas, and hematologic tumors. Carcinomas are the predominant cancers and are cancers of epithelial cells or cells covering the external or internal surfaces of organs, glands, or other body structures (e.g., skin, uterus, lung, breast, prostate, stomach, bowel), and which tend to metastasize. Carcinomas may be adenocarcinomas, for example, of the breast, lung, colon, prostate or bladder, and squamous cell carcinomas. Sarcomas are derived from connective or supportive tissue (e.g., bone, cartilage, tendons, ligaments, fat, and muscle). Sarcomas may be osteosarcomas or osteogenic sarcomas (bone), chondrosarcomas (cartilage), leiomyosarcomas (smooth muscle), rhabdomyosarcomas (skeletal muscle), mesothelial sarcomas or mesotheliomas (membranous lining of body cavities), fibrosarcomas (fibrous tissue), angiosarcomas or hemangioendotheliomas (blood vessels), liposarcomas (adipose tissue), gliomas or astrocytomas (neurogenic connective tissue found in the brain), myxosarcomas (primitive embryonic connective tissue), or mesenchymous or mixed mesodermal tumors (mixed connective tissue types). Hematologic tumors are derived from bone marrow and lymphatic tissue. Hematologic tumors may be myelomas, which originate in the plasma cells of bone marrow; leukemias which may be "liquid tumors" and are tumors of the bone marrow and may be myelogenous or granulocytic leukemia (myeloid and granulocytic white blood cells), lymphatic, lymphocytic, or lymphoblastic leukemias (lymphoid and lymphocytic blood cells) or polycythemia vera or erythremia (various blood cell products, but with red cells predominating); or lymphomas, which may be solid tumors and which develop in the glands or nodes of the lymphatic system, and which may be Hodgkin or Non-Hodgkin lymphomas. In addition, mixed type tumors, such as adenosquamous carcinomas, mixed mesodermal tumors, carcinosarcomas, or teratocarcinomas also exist. All these types of tumors, as well as others that would be apparent to the skilled person, are contemplated in the sense of the present invention.

Tumors that may be treated by the immunological composition of the invention may also be named based on the organ in which they originate i.e., the "primary site," for example, tumor, or cancer, of the breast, brain, lung, liver, skin, prostate, testicle, bladder, colon and rectum, cervix, uterus, etc. This naming often persists even if the tumor metastasizes to another part of the body that is different from the primary site. In this sense, the tumor contemplated in the eight to tenth aspects of the invention may be, but is not limited to, a tumor of the gastrointestinal tract, respiratory system, nervous system, hematopoietic system, epithelium, reproductive system (such as cervical, ovarian, uterine, vaginal, and vulvar), urinary tract, endocrine system, skin, heart, brain, eyes, testes, muscles, bones or breasts. In particular embodiments the tumor contemplated in the eight to tenth aspects of the invention is a tumor of the gastrointestinal tract, respiratory system, hematopoietic system, epithelium, reproductive system (such as cervical, ovarian, uterine, vaginal, and vulvar), urinary tract, endocrine system, skin, heart, muscles, bones or breasts. In a particular embodiment the tumor is a tumor of the colon, lung, liver or breast.

All the embodiments described above for the immunogenic composition of the invention and the pharmaceutical composition comprising it, including embodiments for all its components, also apply to the therapeutic uses described in this section. For example, in particular embodiments the bacterial are whole inactivated bacteria and the combination comprises or consists of *Staphylococcus aureus, Streptococcus pyogenes, Streptococcus pneumoniae, Haemophilus influenzae, Klebsiella pneumoniae*, and *Moraxella catarrhalis*.

In some embodiments the prevention or treatment is autologous. This means that the antigenic determinants contained in the immunogenic composition originate from the same subject being treated. In this case, the immunogenic composition, bacterial population or pharmaceutical composition is for use in a method for preventing or treating a tumor, wherein the method for the prevention and/or treatment comprises the following steps: (i) inactivating tumor cells obtained from a subject, (ii) contacting the inactive tumor cells with the bacterial population to yield an immunogenic composition, (iii) administering the immunogenic composition to the same subject from which the tumor cells were obtained. It is to be understood that steps (i) and (ii) from said method are in vitro.

In other embodiments the treatment is not autologous but allogenic. This means that the antigenic determinants originate from a subject or subjects that are not the subject being treated. In this case, an immunogenic composition as defined in the first aspect of the invention or a bacterial population as defined in the third aspect or a pharmaceutical composition as defined in the fourth aspect is for use in a method for preventing or treating a tumor, wherein the method for the prevention and/or treatment comprises the following steps: (i) inactivating tumor cells of the same type of tumor obtained from a subject or group of subjects, (ii) contacting the inactive tumor cells with the bacterial population to yield an immunogenic composition, (iii) administering the immunogenic composition to a patient suffering from the same type of tumor as in (i). It is to be understood that steps (i) and (ii) from said method are in vitro.

In one embodiment the subjects from which the tumor cells are obtained are HLA matched to the recipient (allogenic treatment). In other embodiments, the tumor cells are from different subject or subjects that are not necessarily HLA matched to the recipient (heterologous treatment).

As mentioned above, the tumor cells may be extracted from the subject or subjects by performing a biopsy. When the tumor cells are not autologous, it is possible to obtain said cells from a pool of biopsied tumor cells or from a tumoral cell line. The tumoral cells are then inactivated to yield whole inactivated cells or a cell lysate, which is subsequently contacted with the bacterial population yielding the immunogenic composition, which is then administered to the patient.

The route of administration may be parenteral. In one embodiment the route of administration is intradermal. In another embodiment the route of administration is subcutaneous. In another embodiment the route of administration is transdermal. In another embodiment the route of administration is intravenous. In another embodiment the route of administration is sublingual. In another embodiment the route of administration is oral.

As shown in the examples below, the immunogenic composition of the invention is capable of preventing growth of a malignant tumor, reducing the size of a malignant tumor and even eliminate a malignant tumor. Therefore, one embodiment of the eight to tenth aspects of the invention is for preventing growth of a malignant tumor. Another embodiment of the eight to tenth aspects of the invention is for preventing cancer. Another embodiment of the eight to tenth aspects of the invention is for treating a malignant tumor. Another embodiment of the eight to tenth aspects of the invention is for treating cancer.

Importantly, it is also shown by the examples below that the immunogenic composition effectively precludes metastasis. Thus, another embodiment of the eight to tenth aspects of the invention is for preventing the growth of a secondary tumor. Another embodiment of the eight to tenth aspects of the invention is for preventing metastasis. Another embodiment of the eight to tenth aspects of the invention is for treating a secondary tumor. Another embodiment of the eight to tenth aspects of the invention is for preventing metastatic cancer.

When used in combination therapy, the combination may be with an antitumoral agent, with radiotherapy or with surgery. More particularly, the immunogenic composition or bacterial populations of the invention are administered separately, in any order, within a therapeutically effective interval with the antitumoral agent, with radiotherapy or with surgery. In a particular embodiment the combination therapy comprises surgery. In another particular embodiment the combination therapy comprises radiation. In a particular embodiment the combination therapy comprises an antitumoral agent. The antitumoral agent may be a cytotoxic agent, such as, for example, alkylating agents, antimetabolites, including folate antagonists, purine and pyrimidine analogues, antibiotics and other natural products, including anthracyclines and *vinca* alkaloids, and antibodies, which improve specificity. The antitumoral agent may also be a hormonal agent or a signal transduction inhibitor. In a particular embodiment the combination therapy comprises chemotherapy. The combination therapy may also comprise a different immunotherapy.

For example, in a particular embodiment the combination may be with monoclonal antibodies blocking immune checkpoint molecules, activated natural killer cells, (CAR) T-cells, tumor-infiltrating lymphocytes or tumor antigen-loaded dendritic cells.

For reasons of completeness, the present invention is also set out in the following numbered embodiments:

1. An immunogenic composition comprising:
   a) a bacterial population comprising at least three pathogenic bacterial species selected from the group consisting of *Staphylococcus aureus, Streptococcus pyogenes, Streptococcus pneumoniae, Haemophilus influenzae, Klebsiella pneumoniae, Staphylococcus epidermidis, Streptococcus viridans, Moraxella catarrhalis, Bordetella pertussis, Neisseria flava, Escherichia coli* and *Proteus mirabilis*, wherein the bacteria are inactivated bacteria, and
   (b) one or more tumor antigenic determinants.

2. The immunogenic composition according to embodiment 1, wherein the bacterial population comprises at least four of the bacterial species.

3. The immunogenic composition according to embodiment 2, wherein the bacterial population comprises at least five of the bacterial species.

4. The immunogenic composition according to any of the embodiment 1-3, wherein the bacterial population comprises *Staphylococcus aureus, Streptococcus pyogenes, Streptococcus pneumoniae, Haemophilus influenzae, Klebsiella pneumoniae*, and *Moraxella catarrhalis*.

5. The immunogenic composition according to claim embodiment 4, wherein the bacterial population consists of *Staphylococcus aureus, Streptococcus pyogenes, Streptococcus pneumoniae, Haemophilus influenzae, Klebsiella pneumoniae*, and *Moraxella catarrhalis*.

6. The immunogenic composition according to embodiment 5, wherein the bacterial population comprises:
from 5 to 25% of *Staphylococcus aureus*,
from 1 to 20% of *Streptococcus pyogenes*,
from 15 to 70% of *Streptococcus pneumoniae*,
from 1 to 30% of *Haemophilus influenzae*,
from 1 to 20% of *Klebsiella pneumoniae*, and
from 1 to 25% of *Moraxella catarrhalis*,
wherein the sum of the percentages for the species in the bacterial population is 100.

7. The immunogenic composition according to the preceding embodiment, wherein the bacterial population comprises:
from 5 to 25% of *Staphylococcus aureus*,
from 1 to 20% of *Streptococcus pyogenes*,
from 15 to 50% of *Streptococcus pneumoniae*,
from 10 to 30% of *Haemophilus influenzae*,
from 1 to 20% of *Klebsiella pneumoniae*, and
from 5 to 25% of *Moraxella catarrhalis*,
wherein the sum of the percentages for the species in the bacterial population is 100.

8. The immunogenic composition according to the preceding embodiment, wherein the bacterial population comprises:
from 10 to 20% of *Staphylococcus aureus*,
from 5 to 15% of *Streptococcus pyogenes*,
from 20 to 40% of *Streptococcus pneumoniae*,
from 15 to 25% of *Haemophilus influenzae*,
from 5 to 15% of *Klebsiella pneumoniae*, and
from 10 to 20% of *Moraxella catarrhalis*,
wherein the sum of the percentages for the species in the bacterial population is 100.

9. The immunogenic composition according to the preceding embodiment, wherein the bacterial population comprises:
15% of *Staphylococcus aureus*,
10% of *Streptococcus pyogenes*,
30% of *Streptococcus pneumoniae*,
20% of *Haemophilus influenzae*,
10% of *Klebsiella pneumoniae*, and
15% of *Moraxella catarrhalis*.

10. The immunogenic composition according to any one of the preceding embodiments, wherein the inactivated bacteria comprise the whole bacterial cell wall.

11. The immunogenic composition according to any of the preceding embodiments, wherein the inactivated bacteria maintain the structural integrity of the bacterial cell.

12. The immunogenic composition according to any of the embodiments 1-9, wherein the inactivated bacteria are lysed bacteria.

13. The immunogenic composition according to any one of the preceding embodiments, wherein the antigenic determinant is in the form of inactivated tumor cells.

14. The immunogenic composition according to the preceding embodiment, wherein the inactivated tumor cells comprise the whole cell membrane.

15. The immunogenic composition according to the preceding embodiment, wherein the inactivated tumor cells maintain the structural integrity of the cell membrane.

16. The immunogenic composition according to embodiment 13, wherein the inactivated tumor cells are lysed cells.

17. The immunogenic composition according to any one of embodiments 1-12, wherein the antigenic determinant is in the form of an isolated antigen.

18. The immunogenic composition according to the preceding embodiment, wherein the isolated antigen is selected from the group consisting of AFP, CEA, HER-2, p53, WT1, and combinations thereof.

19. The immunogenic composition according to any of the embodiments 1-18, wherein the antigenic determinant is from a malignant tumor.

20. The immunogenic composition according to any of the embodiments 1-19, that comprises more than one antigenic determinant and wherein the more than one antigenic determinants are from the same tumor.

21. The immunogenic composition according to any of the embodiments 1-19, that comprises more than one antigenic determinant and wherein the more than one antigenic determinants are from different tumors.

22. The immunogenic composition according to any one of embodiments 1-21, wherein the composition additionally contains a compound selected from a monosaccharide, an amino acid, a fatty acid, a substrate or metabolite of the Krebs cycle, a beta-glucan, a ketonic body, lactate, glyceraldehyde, glycerol, glutamate, and a combination thereof.

23. The immunogenic composition according to the preceding embodiment, wherein the additional compound is selected from the group consisting of glucose, fructose, lactate, glyceraldehyde, lactate, pyruvate, oxalate, malate, glutamate, fumarate, alpha-ketoglutarate, succinate, citrate, glycerol, glutamine, arginine, ketonic bodies, beta-glucans, monounsaturated fatty acids and polyunsaturated fatty acids, and combinations thereof.

24. The immunogenic composition according to the preceding embodiment, wherein the additional compound is selected from the group consisting of glucose, fructose, glutamine, arginine, malate, glutamate, and combinations thereof.

25. The immunogenic composition according to the preceding embodiment, wherein the additional compound is glucose.

26. The immunogenic composition according to any of the embodiments 22-25, wherein the amount of the additional compound is from 0.5 to 10%.

27. The immunogenic composition according to the preceding embodiment, wherein the amount of the additional compound is from 2 to 8%.

28. The immunogenic composition according to the preceding embodiment, wherein the amount of the additional compound is 5%.

29. A bacterial population comprising *Staphylococcus aureus, Streptococcus pyogenes, Streptococcus pneumoniae, Haemophilus influenzae, Klebsiella pneumoniae*, and *Moraxella catarrhalis*, wherein the bacteria are inactivated bacteria.

30. The bacterial population according to the preceding embodiment consisting of *Staphylococcus aureus, Streptococcus pyogenes, Streptococcus pneumoniae, Haemophilus influenzae, Klebsiella pneumoniae, and Moraxella catarrhalis.

31. The bacterial population according to the preceding embodiment, wherein the bacterial population comprises:
from 5 to 25% of Staphylococcus aureus,
from 1 to 20% of Streptococcus pyogenes,
from 15 to 70% of Streptococcus pneumoniae,
from 1 to 30% of Haemophilus influenzae,
from 1 to 20% of Klebsiella pneumoniae, and
from 1 to 25% of Moraxella catarrhalis,
wherein the sum of the percentages for the species in the bacterial population is 100.

32. The bacterial population according to the preceding embodiment, wherein the bacterial population comprises:
from 5 to 25% of Staphylococcus aureus,
from 1 to 20% of Streptococcus pyogenes,
from 15 to 50% of Streptococcus pneumoniae,
from 10 to 30% of Haemophilus influenzae,
from 1 to 20% of Klebsiella pneumoniae, and
from 5 to 25% of Moraxella catarrhalis,
wherein the sum of the percentages for the species in the bacterial population is 100.

33. The bacterial population according to the preceding embodiment, wherein the bacterial population comprises:
from 10 to 20% of Staphylococcus aureus,
from 5 to 15% of Streptococcus pyogenes,
from 20 to 40% of Streptococcus pneumoniae,
from 15 to 25% of Haemophilus influenzae,
from 5 to 15% of Klebsiella pneumoniae, and
from 10 to 20% of Moraxella catarrhalis,
wherein the sum of the percentages for the species in the bacterial population is 100.

34. The bacterial population according to the preceding embodiment, wherein the bacterial population comprises:
15% of Staphylococcus aureus,
10% of Streptococcus pyogenes,
30% of Streptococcus pneumoniae,
20% of Haemophilus influenzae,
10% of Klebsiella pneumoniae, and
15% of Moraxella catarrhalis.

35. The bacterial population according to any of the embodiments 29-34, wherein the inactivated bacteria comprise the whole bacterial cell wall.

36. The bacterial population according to any of the embodiments 29-35, wherein the inactivated bacteria maintain the structural integrity of the bacterial cell.

37. A method for preparing an immunogenic composition comprising contacting one or more tumor antigenic determinants with a bacterial population as defined in any of the embodiments 29-36.

38. The method for preparing an immunogenic composition according to the preceding embodiment, wherein the method comprises the steps of:
(i) inactivating tumor cells, and
(ii) contacting the inactivated tumor cells of step (i) with the bacterial population.

39. The method for preparing an immunogenic composition according to the preceding embodiment, wherein the tumor cells are inactivated by a method that maintains the structural integrity of the cell membrane.

40. The method for preparing an immunogenic composition according to the preceding embodiment, wherein the tumor cells are inactivated by a method selected from the group consisting of phenolization, irradiation and treatment with formalin or formaldehyde.

41. The method for preparing an immunogenic composition according to the preceding embodiment, wherein the tumor cells are inactivated by phenolization.

42. The method for preparing an immunogenic composition according to any of the embodiments 38-41, wherein the tumor cells are from the same type of tumor.

43. The method for preparing an immunogenic composition according to the preceding embodiment, wherein the tumor cells are obtained from a subject or group of subjects.

44. The method for preparing an immunogenic composition according to the preceding embodiment, wherein the tumor cells are obtained from the same subject.

45. The method for preparing an immunogenic composition according to embodiment 42, wherein the tumor cells are from a tumoral cell line.

46. The method for preparing an immunogenic composition according to embodiment 38, wherein the tumor cells are inactivated by lysis.

47. The method for preparing an immunogenic composition according to embodiment 37, wherein the tumor antigenic determinant is in the form of an isolated antigen.

48. The method for preparing an immunogenic composition according to the preceding embodiment, wherein the isolated antigen is selected from the group consisting of AFP, CEA, HER-2, p53, WT1, and combinations thereof.

49. The method for preparing an immunogenic composition according to any of the embodiments 37-48, wherein the tumor is a malignant tumor.

50. The method for preparing an immunogenic composition according to any of the embodiments 37-49, wherein the method comprises a further step (iii) of adding a compound as defined in any of the embodiments 22-25.

51. The method for preparing an immunogenic composition according to the preceding embodiment, wherein the additional compound is added at 0.5 to 10% of the total immunogenic composition.

52. The method for preparing an immunogenic composition according to the preceding embodiment, wherein the additional compound is added at 2 to 8% of the total immunogenic composition, for example at 5% of the total immunogenic composition.

53. A pharmaceutical composition comprising a therapeutically effective amount of an immunogenic composition as defined in any of the embodiments 1-28 or a bacterial population as defined in any of the embodiments 29-36 together with pharmaceutically acceptable excipients and/or or carriers.

54. The pharmaceutical composition according to the preceding embodiment, wherein the composition comprises from 10e7 to 10e12 inactivated bacterial cells/dose.

55. The pharmaceutical composition according to the preceding embodiment, wherein the composition comprises from 10e9 to 10e11 inactivated bacterial cells/dose.

56. The pharmaceutical composition according to any of the embodiments 53-55, wherein the pharmaceutical composition is an intradermal, transdermal, subcutaneous, sublingual, intravenous, nasopharyngeal or oral composition.

57. The pharmaceutical composition according to the preceding embodiment, wherein the pharmaceutical composition is an intradermal composition.

58. The pharmaceutical composition according to the embodiment 56, wherein the pharmaceutical composition is a sublingual composition.

59. The pharmaceutical composition according to any of the embodiments 53-58, further comprising an adjuvant.

60. An immunogenic composition as defined in any of the embodiments 1-28 or a bacterial population as defined in any of the embodiments 29-36, or a pharmaceutical composition as defined in any of the embodiments 53-59 for use as a medicament.

61. An immunogenic composition as defined in any of the embodiments 1-28 or a bacterial population as defined in any of the embodiments 29-36, or a pharmaceutical composition as defined in any of the embodiments 53-59 for use in eliciting a trained innate immune response against a tumor.

62. An immunogenic composition as defined in any of the embodiments 1-28 or a bacterial population as defined in any of the embodiments 29-36, or a pharmaceutical composition as defined in any of the embodiments 53-59 for use in increasing the nonspecific effector response of white blood cells that mediate innate immunity.

63. The immunogenic composition, bacterial population or pharmaceutical composition for use according to the preceding embodiment, wherein the antigen presenting cell is selected from the group consisting of a monocyte, a macrophage, a dendritic cell and combinations thereof.

64. An immunogenic composition as defined in any of the embodiments 1-28 or a bacterial population as defined in any of the embodiments 29-36, or a pharmaceutical composition as defined in any of the embodiments 53-59 for use in a method for the prevention and/or treatment of a tumor.

65. The immunogenic composition, bacterial population or pharmaceutical composition for use according to any of the embodiments 61-64, wherein the tumor is a malignant tumor.

66. The immunogenic composition, bacterial population or pharmaceutical composition for use according to any of the embodiments 61-65, wherein the tumor is a secondary tumor.

67. The immunogenic composition, bacterial population or pharmaceutical composition for use according to any of the embodiments 61-66, wherein the tumor is from the respiratory system, gastrointestinal tract, nervous system, hematopoietic system, reproductive system (such as cervical, ovarian, uterine, vaginal, and vulvar), urinary tract, endocrine system, skin, heart, brain, eyes, testes, muscles, bones or breasts, in particular the tumor is from the respiratory system, gastrointestinal tract, hematopoietic system, reproductive system, urinary tract, endocrine system, skin, heart, muscles, bones or breasts.

68. The immunogenic composition, bacterial population or pharmaceutical composition for use according to the preceding embodiment, wherein the tumor is a breast tumor.

69. The immunogenic composition, bacterial population or pharmaceutical composition for use according to embodiment 67, wherein the tumor is from the gastrointestinal tract.

70. The immunogenic composition, bacterial population or pharmaceutical composition for use according to embodiment 67, wherein the tumor is from the colon.

71. The immunogenic composition, bacterial population or the pharmaceutical composition for use according to any of the embodiments 60-70, wherein the inactivated bacterial cells comprise the whole bacterial cell wall.

72. The immunogenic composition, bacterial population or pharmaceutical composition for use according to the preceding embodiment, wherein the bacterial population comprises *Staphylococcus aureus, Streptococcus pyogenes, Streptococcus pneumoniae, Haemophilus influenzae, Klebsiella pneumoniae* and *Moraxella catarrhalis*.

73. The immunogenic composition, bacterial population or pharmaceutical composition for use according to the preceding embodiment, wherein the bacterial population consists of *Staphylococcus aureus, Streptococcus pyogenes, Streptococcus pneumoniae, Haemophilus influenzae, Klebsiella pneumoniae*, and *Moraxella catarrhalis*.

74. The immunogenic composition, bacterial population or pharmaceutical composition for use according to the preceding embodiment, wherein the bacterial population comprises:
  from 5 to 25% of *Staphylococcus aureus,*
  from 1 to 20% of *Streptococcus pyogenes,*
  from 15 to 50% of *Streptococcus pneumoniae,*
  from 10 to 30% of *Haemophilus influenzae,*
  from 1 to 20% of *Klebsiella pneumoniae*, and
  from 5 to 25% of *Moraxella catarrhalis,*
  wherein the sum of the percentages for the species in the bacterial population is 100.

75. The immunogenic composition, bacterial population or pharmaceutical composition for use according to the preceding embodiment, wherein the bacterial population comprises:
  from 10 to 20% of *Staphylococcus aureus,*
  from 5 to 15% of *Streptococcus pyogenes,*
  from 20 to 40% of *Streptococcus pneumoniae,*
  from 15 to 25% of *Haemophilus influenzae,*
  from 5 to 15% of *Klebsiella pneumoniae*, and
  from 10 to 20% of *Moraxella catarrhalis,*
  wherein the sum of the percentages for the species in the bacterial population is 100.

76. The immunogenic composition, bacterial population or pharmaceutical composition for use according to the preceding embodiment, wherein the bacterial population comprises:
  15% of *Staphylococcus aureus,*
  10% of *Streptococcus pyogenes,*
  30% of *Streptococcus pneumoniae,*
  20% of *Haemophilus influenzae,*
  10% of *Klebsiella pneumoniae*, and
  15% of *Moraxella catarrhalis.*

77. The immunogenic composition, bacterial population or pharmaceutical composition for use according to any of the embodiments 61-76, wherein the method for the prevention and/or treatment comprises the following steps:
  (i) inactivating tumor cells obtained from a subject, (ii) contacting the inactive tumor cells with the bacterial population to yield an immunogenic composition,
  (iii) administering the immunogenic composition to the same subject from which the tumor cells were obtained.

78 The immunogenic composition, bacterial population or pharmaceutical composition for use according to the preceding embodiment, wherein the method for the prevention and/or treatment comprises a further step of adding a compound as defined in any of the embodiments 22-25 to the immunogenic composition.

79. A kit of parts for preparing an immunogenic composition as defined in any of the embodiments 1-28, said kit comprising: (a) a bacterial population as defined in any of the embodiments 29-36.

80. The kit of parts according to the preceding embodiment, further comprising: (b) one or more immunogenic determinants.

81. The kit of parts according to any of the embodiments 79-80, further comprising: (c) a compound as defined in any of the embodiments 22-25.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Furthermore, the present invention covers all possible combinations of particular and preferred embodiments described herein.

EXAMPLES

Example 1. The Combination of Bacterial Population Comprising the Whole Bacterial Cell Wall and Tumor Lysates Induces Specific Antitumoral Immune Response The present study aimed to evaluate the ability of a specific combination of inactivated pathogenic bacteria ("bacterial population") primed with a tumor lysate to induce an innate immune response in order to subsequently develop a specific immune response against solid tumors.

The bacterial population used in this example had the following composition: 15% of Staphylococcus aureus, 10% of Streptococcus pyogenes, 30% of Streptococcus pneumoniae, 20% of Haemophilus influenzae, 10% of Klebsiella pneumoniae, and 15% of Moraxella catarrhalis. The combination was provided by Laboratorios Diater S.A. The bacterial population was inactivated by phenolization.

CT26.CL25 cells were obtained from ATCC® CRL-2639 ™. These are mouse derived cells (Mus musculus, lineage Balb/c) with fibroblastic morphology that grow in adherence. These cells are derived from a Balb/c mouse-induced colon carcinoma by the ability to transform of T-antigen SV40 virus). CT-26 cells, once injected into Balb/c mice, are capable of inducing solid tumors with similar characteristics as the tumors from which they originate. For this reason, CT-26 cells are commonly used as a model to test immunotherapy protocols as well as studies of the development of host immune responses.

Glucose was obtained from Sigma-Aldrich (G8270).

CT26.CL25 cell lysate was prepared by subjecting a pellet of 0.5×10e6 CT26.CL25 cells (ATCC® CRL-2639 ™) to three rounds of freezing (−80° C.) and thawing (37° C.).

The immunogenic composition was prepared by mixing by pipetting the lysate derived from 0.5×10e6 CT26.CL25 cells with 50 uL (10e8/mL) of phenol-inactivated bacterial population at room temperature and was kept on ice until use.

CT-26 cells were subcutaneously inoculated (0.5×10e6/mice) into 12 week-old male Balb/c mice. After 16 days, the cells injected generated subcutaneous tumors that showed 5×5 mm in size. At this time, the mice were divided into the following 4 experimental groups:

GROUP 1.—Control: administration of 50 uL of saline on the contralateral side of the tumor.
GROUP 2.—Bacterial population: administration of 50 uL (10e8/mL) of bacterial population on the contralateral side of the tumor
GROUP 3.—immunogenic composition: administration of 50 uL of bacterial population (10e8/mL) in combination with tumor lysate (obtained from 0.5×10e6 CT-26 cells) on the contralateral side of the tumor
GROUP 4.—immunogenic composition with glucose: administration of 50 uL of bacterial population (10e8/mL) in combination with tumor lysate (obtained from 0.5×10e6 CT-26 cells)+5% glucose on the contralateral side of the tumor.

Subsequently, the size of the subcutaneous tumors induced in the mice included in the different experimental groups were determined weekly, as shown in FIG. 1A.

The results obtained demonstrate that the administration of the bacterial population on the side contralateral to the tumor (Group 2) is not capable of inducing an immune response against the tumor induced by subcutaneous administration of CT-26 cells, since the growth rate it is similar to the control group (who received saline, Group 1). Mice that received the bacterial population in combination with a CT-26 cell tumor lysate (Group 3) were able to prevent the growth of implanted tumors (see detail in FIG. 1A), with 2 of the 5 mice included in this group showing complete remissions. The administration of a combination of bacterial population together with a CT-26 cell tumor lysate supplemented with 5% glucose (Group 4) turned out to be even more effective (see detail in FIG. 1A), since they show a smaller tumor size than the Group 3 and also 3 of the 5 mice included in this group showed complete remissions.

On the other hand, in order to evaluate the development of a specific antitumor response with the capacity to develop an immunological memory response, in experimental groups 3 and 4, the CT-26 tumor line (0.5×10e6 cells per mouse) was re-injected on the contralateral side to which the initial tumor was injected). The generation of a de novo tumor (secondary tumor) was not observed in any of the mice included in these two experimental groups, indicating that these mice had developed a specific memory response to the tumor, thus being protected against new challenges with this type of tumor.

Example 2. The Combination of Bacterial Population Comprising the Whole Bacterial Cell Wall and Tumor Lysates Prevents the Development of Tumors Also, we tested the ability of the CT-26 cell tumor lysate together with the combination of the phenol-inactivated bacterial population as defined in example 1 to exert a preventive immune response (vaccination) against this tumor. For this, male balb/c mice were divided in the following experimental groups:

GROUP 1.—Bacterial population: subcutaneous administration of 50 uL (10e8 cfu/mL) of bacterial population.
GROUP 2.—Tumor lysate control: subcutaneous administration of tumor lysate obtained from 0.5×10e6 CT-26 cells.
GROUP 3.—Immunogenic tumor vaccination: subcutaneous administration of 50 uL of bacterial population (10e8 cfu/mL) in combination with tumor lysate (obtained from 0.5×10e6 CT-26 cells).

Two weeks after administering the bacterial population (GROUP 1), tumor lysate (GROUP 2), or immunogenic composition (GROUP 3), all the experimental groups were inoculated subcutaneous with 0.5×10e6 CT-26 cells in order to induce tumors. The results obtained showed that, after two weeks of inoculation of the tumor cells, the mice included in the experimental Groups 1 and 2 developed subcutaneous tumors with a size greater than 1 cm in diameter, while Group 3 did not observe any tumor formation. These results indicate that the combination of the tumor lysate together with the inactivated bacteria is capable of protecting the subsequent development of a tumor generated with the cells used to obtain the tumor lysate, suggesting a tumor vaccination effect and thus reinforcing the memory immune response already demonstrated in the first experiments carried out.

Example 3. The Combination of Bacterial Population Comprising the Whole Bacterial Cell Wall and Tumor Lysates Elicits a Specific Antitumoral Immune Response in Dogs In a third series of experiments, we tested the efficacy of the combination of tumor lysates in combination with phenol-inactivated bacterial population as defined in example 1 for the treatment of breast tumors in dogs. For this, independent biopsies (of approximately 2.5 cm in diameter) were obtained from surgically removed breast carcinomas from two different dogs. In order to generate a tumor lysate, the biopsies were subjected to three rounds of freezing (−80° C.) and thawing (37° C.). After the last freeze-thaw round, 1.5 mL of tumor lysate was obtained, which was frozen in three independent aliquots, each containing 0.5 mL of tumor lysate.

Three doses of immunogenic composition were administered to the recipient animals by subcutaneous injection with a 2-week gap between each dose. Each dose was prepared prior to administration by thawing a 500 ul aliquot in and combining it with 500 uL (10e8 cfu/mL) of phenol-inactivated bacterial population. Each animal received the immunogenic composition prepared with tumor cells biopsied from its own breast carcinoma (autologous treatment). No adverse reaction was observed either during subcutaneous injection of the combination of tumor lysate together with the inactivated bacteria, or on subsequent days after each administration. After 6 months, the two animals are still free from the development of breast cancer.

In summary, the results obtained demonstrate that:

1. The bacterial population comprising whole bacterial cell walls was capable of generating a specific antitumoral immune response as long as combined with antigens derived from the tumor (see results Groups 3 and 4, FIG. 1). Tumor antigens from the tumor lysate would act by directing the nonspecific immune response generated by bacterial population.

2. The administration of a bacterial population alone is not capable of generating an antitumor response (see results Group 2, FIG. 1).

3. Supplementation with glucose (5%) of the immunological composition containing the bacterial population and the tumor lysate enhances the specific anti-tumor response generated by the bacterial population+tumor lysate (see results Group 4, FIG. 1). It is hypothesized that the addition of glucose in the environment in which the anti-tumor immune response is to be initiated would help its development thanks to the contribution of energy to those cells that intervene in this process (mainly antigen-presenting cells that are metabolically very active and require a great contribution of energy during the phagocytosis process and antigen processing for presentation to specific cells of the immune system).

4. The combination of bacterial vaccines together with tumor lysates (in the presence or not of glucose) is capable of developing a memory response against the tumor (see results Groups 3 and 4, FIG. 2).

5. The combination of bacterial population and tumor lysate elicits a preventive immune response against tumors. The combination is therefore effective as a tumor vaccine.

6. The combination of bacterial population and tumor lysate generates a specific antitumoral immune response in dogs.

CITATION LIST

Saeed et al. Epigenetic programming of monocyte-to-macrophage differentiation and trained innate immunity. Science 2014, Vol. 345, Issue 6204, 1251086, DOI: 10.1126/science.1251086

Fan et al. Inactivation of Gram-Positive Bacteria by Novel Phenolic Branched-Chain Fatty Acids. J Food Prot, 2017, vol 80, issue 1, p. 6-14. doi: 10.4315/0362-028X.JFP-16-080.

Levinson et al, Production of potent inactivated vaccines with ultraviolet irradiation: ii. an abbreviated preliminary report on sterilization of bacteria and immunization with rabies and St. Louis encephalitis vaccines. JAMA 1944; 125(8): 531-532. doi:10.1001/jama.1944.02850260005002.

Hankaniemi et al, Formalin treatment increases the stability and immunogenicity of coxsackievirus B1 VLP vaccine. Antiviral Research 2019, Volume 171, 104595.

Novellino, et al, A listing of human tumor antigens recognized by T cells. Cancer Immunol Immunother 2005, vol 54, p. 187-207. DOI: 10.1007/s00262-004-0560-6.

What is claimed is:

1. An immunogenic composition comprising:
   a) a bacterial population comprising *Staphylococcus aureus, Streptococcus pyogenes, Streptococcus pneumoniae, Haemophilus influenzae, Klebsiella pneumoniae,* and *Moraxella catarrhalis,* wherein the bacteria are whole inactivated bacteria that retain the integrity of their bacterial cell wall, and
   b) one or more tumor antigenic determinants.

2. The immunogenic composition according to claim 1, wherein the bacterial population consists of *Staphylococcus aureus, Streptococcus pyogenes, Streptococcus pneumoniae, Haemophilus influenzae, Klebsiella pneumoniae,* and *Moraxella catarrhalis.*

3. The immunogenic composition according to claim 1, wherein the bacterial population comprises:
   from 5 to 25% of *Staphylococcus aureus,*
   from 1 to 20% of *Streptococcus pyogenes,*
   from 15 to 70% of *Streptococcus pneumoniae,*
   from 1 to 30% of *Haemophilus influenzae,*
   from 1 to 20% of *Klebsiella pneumoniae,* and
   from 1 to 25% of *Moraxella catarrhalis,*
   wherein the sum of the percentages for the species in the bacterial population is 100.

4. The immunogenic composition according to claim 1, wherein the antigenic determinant is in the form of inactive tumor cells.

5. The immunogenic composition according to claim 1, wherein the composition additionally contains a compound selected from the group consisting of glucose, fructose, lactate, glyceraldehyde, lactate, pyruvate, oxalate, malate, glutamate, fumarate, alpha-ketoglutarate, succinate, citrate, glycerol, glutamine, arginine, ketonic bodies, beta-glucans, monounsaturated fatty acids and polyunsaturated fatty acids, and combinations thereof.

6. The immunogenic composition according to claim 5, wherein the additional compound is glucose.

7. The immunogenic composition according to claim 1, further comprising pharmaceutically acceptable excipients and/or or carriers.

8. A method for preventing and/or treating a tumor, the method comprising administering to a subject in need thereof a therapeutically effective amount of the immunogenic composition as defined in claim 1.

9. The method according to claim 8, wherein the tumor is a malignant tumor.

10. The method according to claim 8, wherein the administration of the immunogenic composition prevents or inhibits tumor metastasis.

11. A method for preventing and/or treating a tumor, the method comprising administering to a subject in need thereof a therapeutically effective amount of a bacterial population comprising *Staphylococcus aureus, Streptococcus pyogenes, Streptococcus pneumoniae, Haemophilus influenzae, Klebsiella pneumoniae*, and *Moraxella catarrhalis*, wherein the bacteria are whole inactivated bacteria that retain the integrity of their bacterial cell wall, in combination with one or more tumor antigenic determinants, wherein the bacterial population and the one or more tumor antigenic determinants are administered simultaneously, sequentially or separately within a therapeutic interval.

12. The method according to claim 11, wherein the bacterial population consists of *Staphylococcus aureus, Streptococcus pyogenes, Streptococcus pneumoniae, Haemophilus influenzae, Klebsiella pneumoniae*, and *Moraxella catarrhalis*.

13. The method according to claim 11, wherein the bacterial population comprises:
- from 5 to 25% of *Staphylococcus aureus*,
- from 1 to 20% of *Streptococcus pyogenes*,
- from 15 to 70% of *Streptococcus pneumoniae*,
- from 1 to 30% of *Haemophilus influenzae*,
- from 1 to 20% of *Klebsiella pneumoniae*, and
- from 1 to 25% of *Moraxella catarrhalis*,
- wherein the sum of the percentages for the species in the bacterial population is 100.

14. The method according to claim 11, wherein the one or more antigenic determinant is in the form of inactive tumor cells.

15. The method according to claim 11, wherein the prevention and/or treatment further comprises simultaneous, sequential or separate administration within a therapeutic interval of a compound selected from the group consisting of glucose, fructose, lactate, glyceraldehyde, lactate, pyruvate, oxalate, malate, glutamate, fumarate, alpha-ketoglutarate, succinate, citrate, glycerol, glutamine, arginine, ketonic bodies, beta-glucans, monounsaturated fatty acids and polyunsaturated fatty acids, and combinations thereof.

16. The method according to claim 15, wherein the compound is glucose.

17. The method according to claim 11, wherein the administration is simultaneous.

18. The method according to claim 11, wherein the tumor is a malignant tumor.

19. The method according to claim 18, wherein the administration of the bacterial population and the one or more tumor antigenic determinants prevents or inhibits tumor metastasis.

20. The method according to claim 11, the method comprising the following steps:
  (i) inactivating tumor cells obtained from a subject,
  (ii) contacting the inactive tumor cells with a bacterial population a bacterial population comprising *Staphylococcus aureus, Streptococcus pyogenes, Streptococcus pneumoniae, Haemophilus influenzae, Klebsiella pneumoniae*, and *Moraxella catarrhalis*, wherein the bacteria are inactivated bacteria comprising the whole bacterial cell wall, to provide an immunogenic composition,
  (iii) optionally adding to the immunogenic composition of step (ii) a compound selected from the group consisting of glucose, fructose, lactate, glyceraldehyde, lactate, pyruvate, oxalate, malate, glutamate, fumarate, alpha-ketoglutarate, succinate, citrate, glycerol, glutamine, arginine, ketonic bodies, beta-glucans, monounsaturated fatty acids and polyunsaturated fatty acids, and combinations thereof, and
  (iv) administering the immunogenic composition of steps (ii) or (iii) to the same subject from which the tumor cells were obtained.

21. The method according to claim 8, wherein the administration is prevention of a colon cancer.

22. The method according to claim 11, wherein the administration is prevention of a colon cancer.

* * * * *